(12) United States Patent
Khairkhahan et al.

(10) Patent No.: US 9,020,611 B2
(45) Date of Patent: Apr. 28, 2015

(54) LEADLESS CARDIAC PACEMAKER WITH ANTI-UNSCREWING FEATURE

(75) Inventors: Alexander Khairkhahan, Palo Alto, CA (US); Eric Varady, San Francisco, CA (US); Kenneth J. Carroll, Los Altos, CA (US); Paul Paspa, Los Gatos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 45 days.

(21) Appl. No.: 13/272,082

(22) Filed: Oct. 12, 2011

(65) Prior Publication Data

US 2012/0116489 A1    May 10, 2012

Related U.S. Application Data

(60) Provisional application No. 61/392,886, filed on Oct. 13, 2010, provisional application No. 61/422,618, filed on Dec. 13, 2010.

(51) Int. Cl.
*A61N 1/375* (2006.01)
*A61N 1/05* (2006.01)
*A61N 1/372* (2006.01)

(52) U.S. Cl.
CPC .............. *A61N 1/375* (2013.01); *A61N 1/0573* (2013.01); *A61N 1/37205* (2013.01); *A61N 1/3756* (2013.01)

(58) Field of Classification Search
CPC ..... A61N 1/057; A61N 1/0573; A61N 1/375; A61N 1/3756
USPC .......................... 607/116, 119, 122, 126–127
See application file for complete search history.

(56) References Cited

U.S. PATENT DOCUMENTS

| 3,199,508 A | 8/1965 | Roth |
| 3,212,496 A | 10/1965 | Preston |
| 3,218,638 A | 11/1965 | Honig |

(Continued)

FOREIGN PATENT DOCUMENTS

| EP | 1741465 A1 | 1/2007 |
| JP | H04-506167 A | 10/1992 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — Catherine Voorhees
(74) *Attorney, Agent, or Firm* — Theresa A. Raymer

(57) ABSTRACT

A leadless cardiac pacemaker comprises a housing, a plurality of electrodes coupled to an outer surface of the housing, and a pulse delivery system hermetically contained within the housing and electrically coupled to the electrode plurality, the pulse delivery system configured for sourcing energy internal to the housing, generating and delivering electrical pulses to the electrode plurality. The pacemaker further comprises an anti-unscrewing feature disposed on either a fixation device of the pacemaker or on the housing itself. The anti-unscrewing feature can be configured to prevent the fixation device from disengaging the wall of the heart.

20 Claims, 20 Drawing Sheets

(56) References Cited

U.S. PATENT DOCUMENTS

| | | |
|---|---|---|
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |

(56) References Cited

U.S. PATENT DOCUMENTS

| | | |
|---|---|---|
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |

(56) References Cited

U.S. PATENT DOCUMENTS

| | | |
|---|---|---|
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |

(56) References Cited

U.S. PATENT DOCUMENTS

| | | |
|---|---|---|
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0230282 A1* | 11/2004 | Cates et al. ............... 607/126 |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1* | 2/2005 | Haack ............... 607/126 |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0123923 A1 | 5/2007 | Lindstrom et al. |
| 2007/0142709 A1 | 6/2007 | Martone et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0109054 A1* | 5/2008 | Hastings et al. ............... 607/127 |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1* | 1/2009 | Hastings et al. ............... 607/32 |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2009/0204170 A1 | 8/2009 | Hastings et al. |
| 2010/0069983 A1 | 3/2010 | Peacock et al. |
| 2010/0198288 A1* | 8/2010 | Ostroff ............... 607/9 |
| 2010/0211149 A1* | 8/2010 | Morgan et al. ............... 607/127 |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0218587 A1 | 9/2011 | Jacobson |
| 2011/0282423 A1 | 11/2011 | Jacobson |
| 2012/0245665 A1* | 9/2012 | Friedman et al. ............... 607/127 |
| 2013/0041422 A1 | 2/2013 | Jacobson |

FOREIGN PATENT DOCUMENTS

| | | |
|---|---|---|
| JP | 05-245215 | 9/1993 |
| JP | 06/507096 | 3/2006 |
| JP | 06/516449 | 7/2006 |
| JP | 2006-526483 A | 11/2006 |
| WO | WO 93/12714 A1 | 7/1993 |
| WO | WO02/34333 A2 | 5/2002 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |
| WO | WO2010/088116 A1 | 8/2010 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Löchinger ; Safety aspects of cardiac pacemakers in magnetic resonance imaging; Dissertation submitted to the Swiss Federal Institute of Technology Zurich; 137 pages; 2002 (month unavailable).

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: In vitro assessment at 1.5 T; Am Heart J; vol. 151; No. 2; pp. 436-443; Feb. 2006.

Khairkhahan et al.; U.S. Appl. No. 13/272,074 entitled "Delivery catheter systems and methods," filed Oct. 12, 2011.

Ostroff, Alan; U.S. Appl. No. 13/272,092 entitled "Temperature sensor for a leadless cardiac pacemaker," filed Oct. 12, 2011.

Khairkhahan et al.; U.S. Appl. No. 13/324,781 entitled "Delivery Catheter Systems and Methods," filed Dec. 13, 2011.

Jacobson et al.; U.S. Appl. No. 13/277,151 entitled "Leadless cardiac pacemaker with conducted communication," filed Oct. 19, 2011.

Khairkhahan et al.; U.S. Appl. No. 13/324,802 entitled "Pacemaker Retrieval Systems and Methods ," filed Dec. 13, 2011.

Khairkhahan et al.; U.S. Appl. No. 13/331,922 entitled "Leadless Pacemaker with Radial Fixation Mechanism ," filed Dec. 20, 2011.

Jacobson, Peter M.; U.S. Appl. No. 13/708,732 entitled "Leadless Cardiac Pacemaker Triggered by Conductive Communication," filed Dec. 7, 2012.

Varady et al.; U.S. Appl. No. 13/669,242 entitled "Leadless Cardiac Pacemaker with Integral Battery and Redundant Welds," filed Nov. 5, 2012.

Jacobson, P.; U.S. Appl. No. 13/866,803 entitled "Leadless cardiac pacemaker system for usage in combination with an implantable cardioverter-defribrillator," filed Apr. 19, 2013.

(56) References Cited

OTHER PUBLICATIONS

Pertijs et al.; U.S. Appl. No. 13/901,414 entitled "Temperature Sensor for a Leadless Cardiac Pacemaker," filed May 23, 2013.
Ostroff et al.; U.S. Appl. No. 13/910,896 entitled "Leadless Pacemaker with Multiple Electrodes," filed Jun. 5, 2013.
Ostroff, Alan; U.S. Appl. No. 13/915,560 entitled "MRI Compatible Leadless Cardiac Pacemaker," filed Jun. 11, 2013.
Carroll et al.; U.S. Appl. No. 13/956,946 entitled "Biostimulator Circuit with Flying Cell," filed Aug. 1, 2013.
Ostroff, Alan; U.S. Appl. No. 13/967,180 entitled "Leadless Cardiac Pacemaker with Secondary Fixation Capability" filed Aug. 14, 2013.
Ostroff et al; U.S. Appl. No. 13/972,828 entitled "X-Ray Identification for Active Implantable Medical Device" filed Aug. 21, 2013.

* cited by examiner

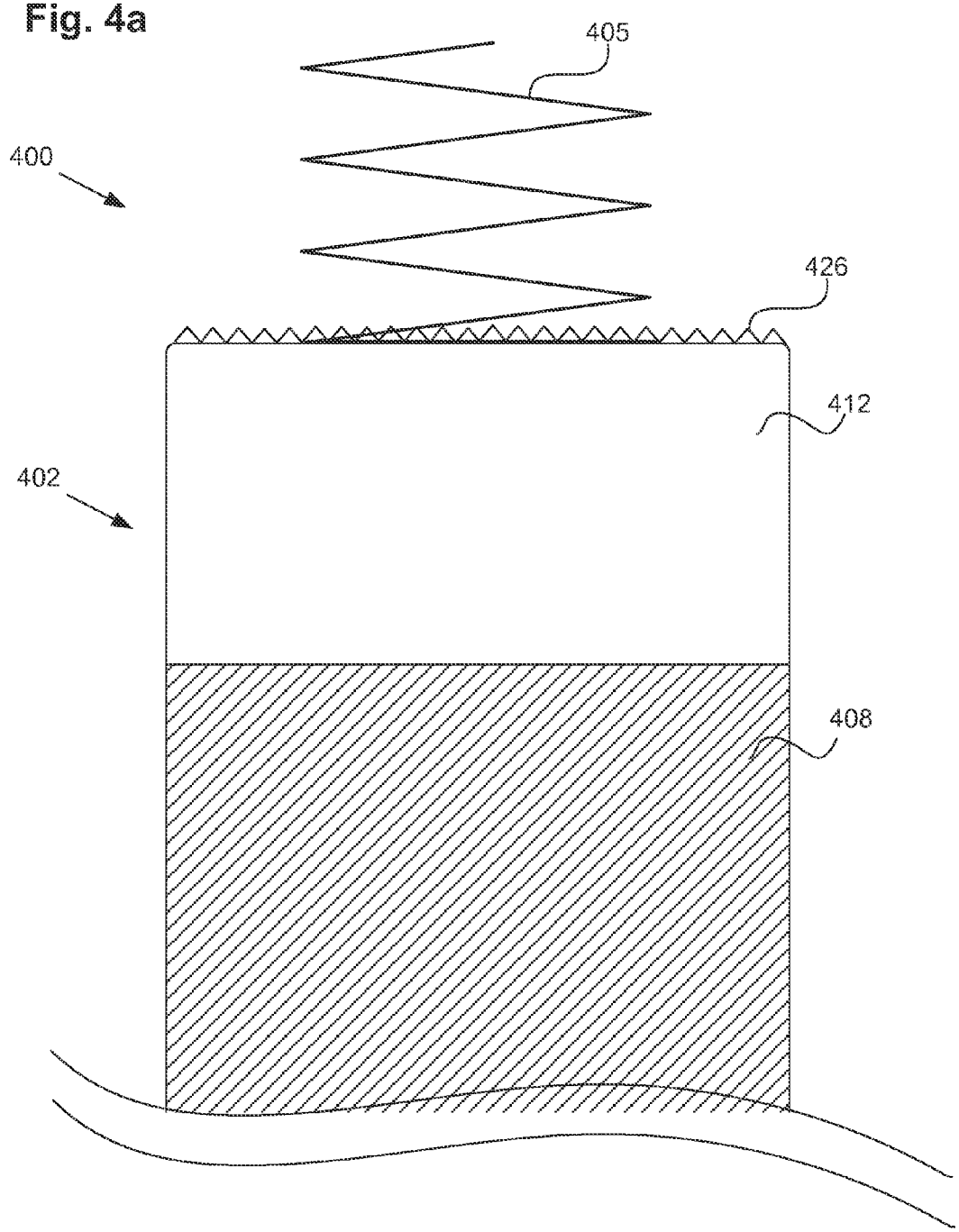

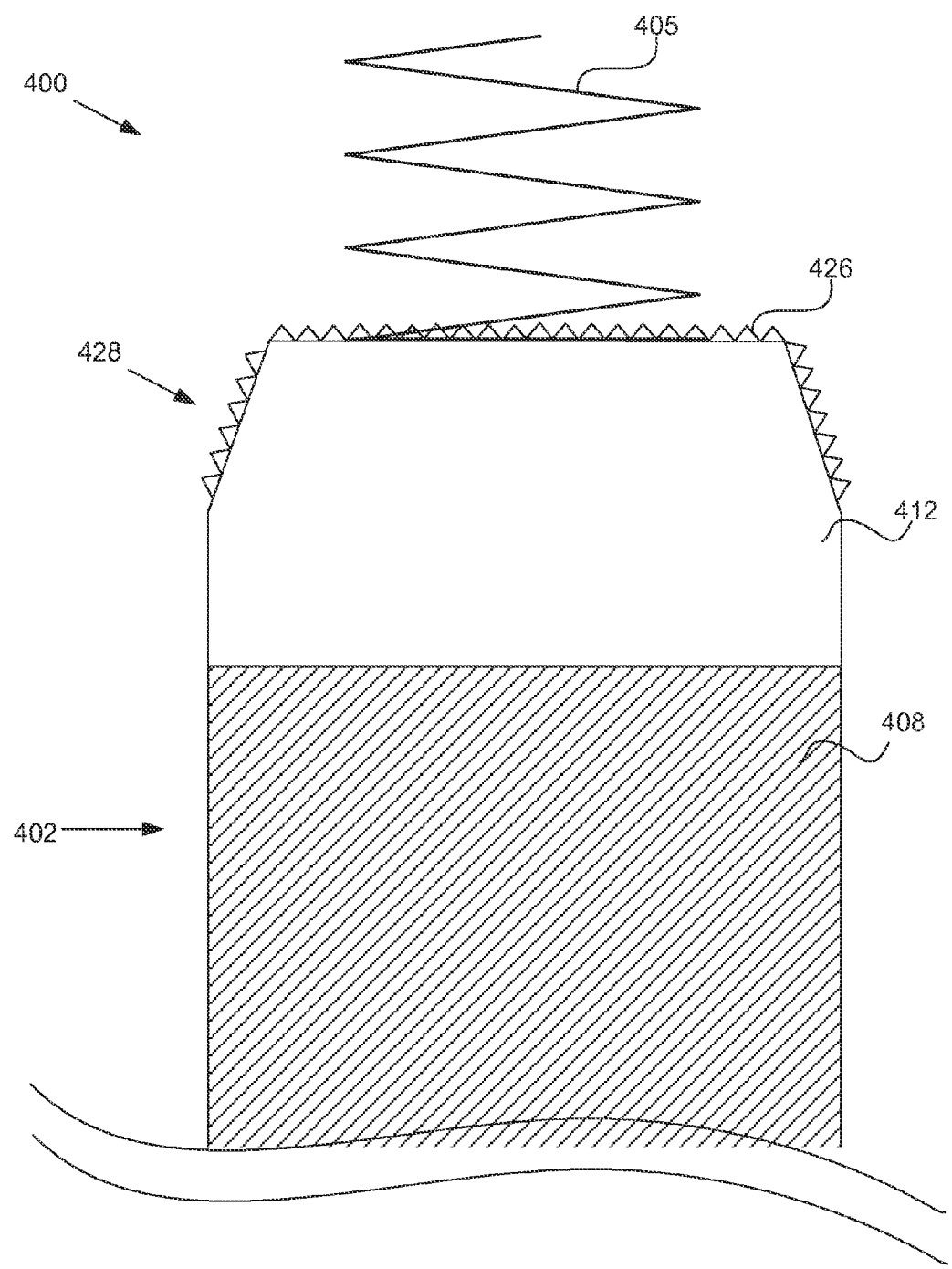

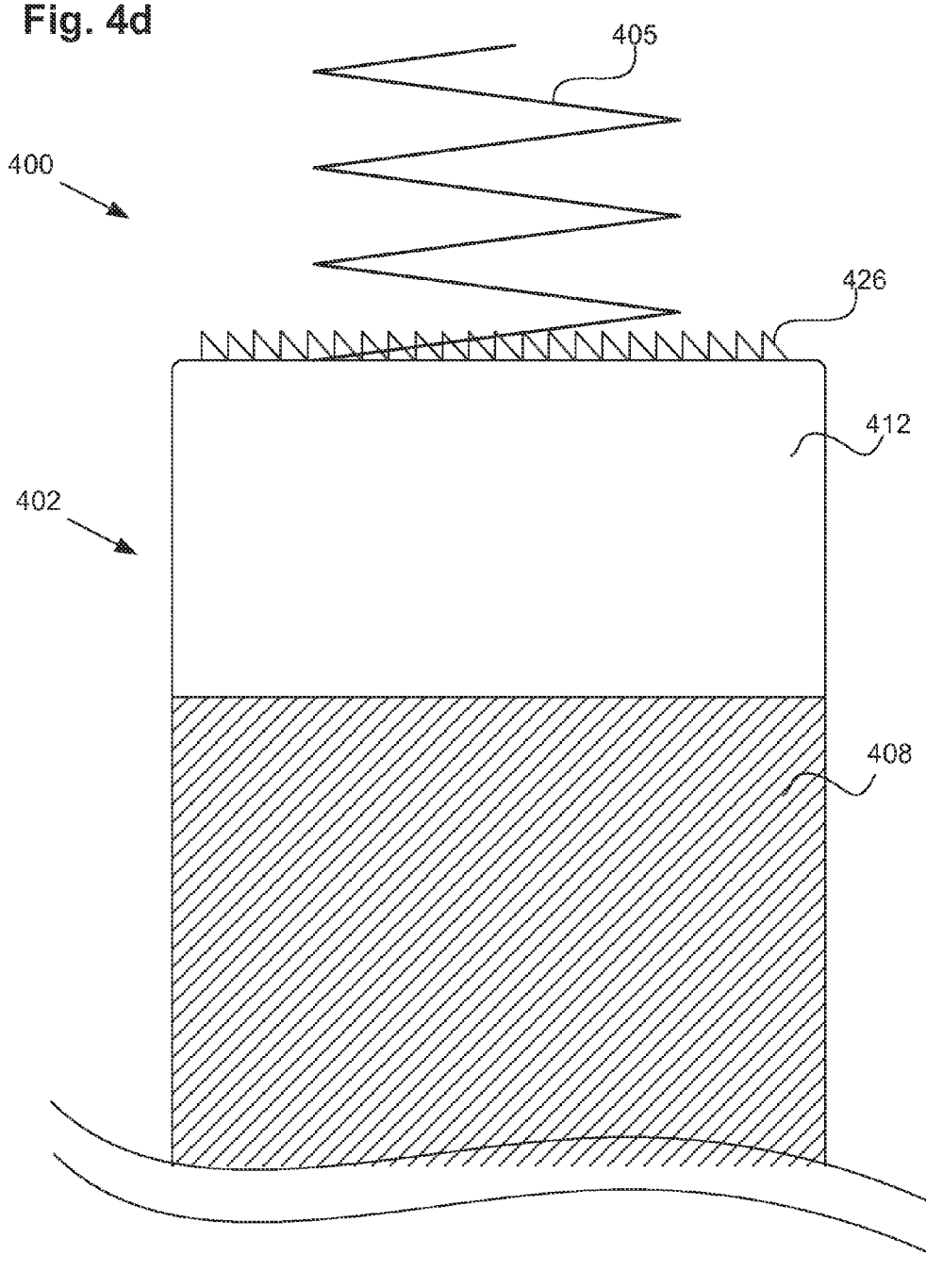

LEADLESS CARDIAC PACEMAKER WITH ANTI-UNSCREWING FEATURE

CROSS REFERENCE TO RELATED APPLICATIONS

This application claims the benefit under 35 U.S.C. 119 of U.S. Provisional Patent Application No. 61/392,886, filed Oct. 13, 2010, titled "Leadless Cardiac Pacemaker with Anti-Unscrewing Feature", and U.S. Provisional Patent Application No. 61/422,618, filed Dec. 13, 2010, titled "Leadless Cardiac Pacemaker with Anti-Unscrewing Feature", both of which are incorporated herein by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present disclosure relates to leadless cardiac pacemakers, and more particularly, to features and methods by which they are affixed within the heart. More specifically, the present disclosure relates to features and methods for preventing a leadless cardiac pacemaker from unscrewing itself out of tissue.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium.

The potential of detachment of the leadless biostimulator from the implant site would represent an immediately serious event, as for example, a pacemaker lost from the right ventricle can exit the heart via the pulmonic valve and lodge in the lung.

SUMMARY OF THE DISCLOSURE

A leadless biostimulator is provided, comprising a housing sized and configured to be implanted within a heart of a patient, a primary fixation device attached to the housing and configured to affix the biostimulator to a wall of the heart, and an anti-unscrewing feature disposed on the primary fixation device, the anti-unscrewing feature configured to prevent the primary fixation device from disengaging the wall of the heart.

In some embodiments, the primary fixation device is a fixation helix.

In other embodiments, the anti-unscrewing feature is at least one barb. In some embodiments, the at least one barb is pointed generally proximally away from a distal end of the fixation device.

In some embodiments, a first torque required to insert the fixation device into the wall of the heart is less than a second torque required to remove the fixation device from the wall of the heart.

In some embodiments, the anti-unscrewing feature is at least one rounded feature. In other embodiments, the anti-unscrewing feature is at least one through-hole. In additional embodiments, the anti-unscrewing feature is at least one depression.

A leadless biostimulator is provided, comprising a housing sized and configured to be implanted within a heart of a patient, a primary fixation helix attached to the housing and configured to affix the biostimulator to a wall of the heart, and an anti-unscrewing helix wound in an opposite direction of the primary fixation helix, the anti-unscrewing helix attached to the housing.

In some embodiments, the primary fixation helix is a right-handed helix and the anti-unscrewing helix is a left-handed helix. In other embodiments, the primary fixation helix is longer than the anti-unscrewing helix. In additional embodiments, the anti-unscrewing helix is positioned outside of the primary fixation helix.

In some embodiments, the primary fixation helix is an electrode.

In other embodiments, the anti-unscrewing helix is configured to compress against tissue as the primary fixation helix is affixed to the wall of the heart.

The leadless biostimulator of claim 9 wherein the anti-unscrewing helix is configured to engage the wall of the heart in the event the biostimulator unscrews from the wall of the heart.

A leadless biostimulator, comprising: a housing sized and configured to be implanted within a heart of a patient; a primary fixation device attached to the housing and configured to affix the biostimulator to a wall of the heart; and an anti-unscrewing feature disposed on the housing, the anti-unscrewing feature configured to prevent the primary fixation device from disengaging the wall of the heart.

In some embodiments, the primary fixation device comprises a fixation helix.

In some embodiments, the anti-unscrewing feature comprises a plurality of teeth, barbs, or other sharpened features. In many embodiments, the teeth, barbs, or other sharpened features are disposed on a distal surface of the housing. In some embodiments, the teeth, barbs, or other sharpened features are disposed on a tapered surface of the housing. In other embodiments, the teeth, barbs, or other sharpened features are arranged asymmetrically to provide resistance only in an unscrewing direction of the primary fixation device.

In one embodiment, a first torque required to insert the fixation device into the wall of the heart is less than a second torque required to remove the fixation device from the wall of the heart.

In some embodiments, the anti-unscrewing feature is a cleat. In one embodiment, the cleat is positioned on the housing beneath the fixation device. In other embodiments, the cleat is directed towards the fixation device and configured to grab heart tissue between the cleat and the fixation device to resist unintentional detachment of the fixation device from the wall of the heart.

In some embodiments, the anti-unscrewing feature is at least one through-hole. In other embodiments, the anti-unscrewing feature is at least one depression.

A leadless biostimulator is provided, comprising a housing sized and configured to be implanted within a heart of a patient, a primary fixation device attached to the housing and configured to affix the biostimulator to a wall of the heart, and at least one through-hole disposed in the housing, the at least one through-hole configured to promote tissue in-growth into the through-hole to prevent the primary fixation device from disengaging the wall of the heart.

In some embodiments, the at least one through-hole extends horizontally into the housing. In other embodiments, the at least one through-hole extends along a longitudinal axis of the housing. In some embodiments, the at least one through-hole has a diameter of approximately 0.005" to 0.04". In other embodiments, the at least one through-hole extends partially across a diameter of the housing. In additional embodiments, the at least one through-hole extends fully across a diameter of the housing. In some embodiments, the at least one through-hole is filled with a bioabsorbable material.

A method of preventing unintentional detachment of a leadless biostimulator from a heart of a patient is provided, comprising applying torque to the leadless biostimulator in a first direction to affix the leadless biostimulator to heart tissue with a primary fixation device, applying torque to the tissue in a second direction with an anti-unscrewing device to prevent disengagement of the leadless biostimulator from tissue.

In some embodiments, the torque in the second direction is greater than the torque in the first direction.

A method of preventing detachment of a leadless biostimulator from a patient is provided, comprising implanting the leadless biostimulator into heart tissue of the patient, preventing the leadless biostimulator from detaching from the heart tissue with a bioabsorbable anti-unscrewing feature, and allowing the bioabsorbable anti-unscrewing feature to be absorbed by the patient in less than 3 months.

In some embodiments, the anti-unscrewing feature is a suture. In additional embodiments, the suture is bio-absorbable.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4a-4f illustrate embodiments of anti-unscrewing features disposed on a housing of a leadless cardiac pacemaker.

DETAILED DESCRIPTION OF THE INVENTION

Figure 1:
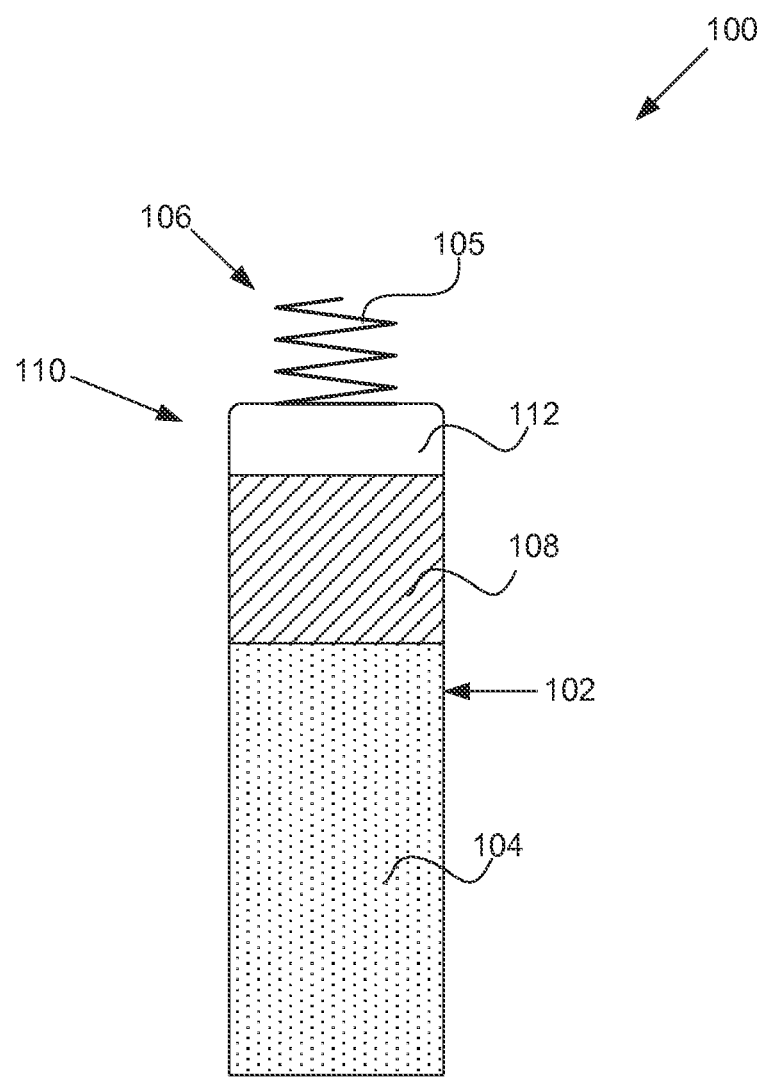
FIG. 1 illustrates one embodiment of a leadless cardiac pacemaker or biostimulator.

A leadless cardiac pacemaker can communicate by conducted communication, representing a substantial departure from conventional pacing systems. For example, an illustrative cardiac pacing system can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

Various embodiments of a system comprising one or more leadless cardiac pacemakers or biostimulators are described. An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

FIG. 1 shows a leadless cardiac pacemaker or leadless biostimulator 100. The biostimulators can include a hermetic housing 102 with electrodes 104 and 106 disposed thereon. As shown, electrode 106 can be disposed on or integrated within a fixation device 105, and the electrode 104 can be disposed on the housing 102. The fixation device 105 can be a fixation helix or other flexible or rigid structure suitable for attaching the housing to tissue, such as heart tissue. In other embodiments, the electrode 106 may be independent from the fixation device in various forms and sizes. The housing can also include an electronics compartment 110 within the housing that contains the electronic components necessary for operation of the biostimulator. The hermetic housing can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In the embodiment of FIG. 1, a single insulator 108 is disposed along the portion of the housing between electrodes 104 and 106. In some embodiments, the housing itself can comprise an insulator instead of a conductor, such as an alumina ceramic or other similar materials, and the electrodes can be disposed upon the housing.

As shown in FIG. 1, the biostimulator can further include a header assembly 112 to isolate electrode 104 from electrode 106. The header assembly 112 can be made from tecothane or another biocompatible plastic, and can contain a ceramic to metal feedthrough, a glass to metal feedthrough, or other appropriate feedthrough insulator as known in the art.

The electrodes 104 and 106 can comprise pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In FIG. 1, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A helical fixation device 105, can enable insertion of the device endocardially or epicardially through a guiding catheter. A torqueable catheter can be used to rotate the housing and force the fixation device into heart tissue, thus affixing the fixation device (and also the electrode 106 in FIG. 1) into contact with stimulable tissue. Electrode 104 can serve as an indifferent electrode for sensing and pacing. The fixation device may be coated partially or in full for electrical insulation, and a steroid-eluting matrix may be included on or near the device to minimize fibrotic reaction, as is known in conventional pacing electrode-leads.

Various anti-unscrewing features can be included on the biostimulator to provide a feature that requires that the torque necessary to unscrew the biostimulator from tissue is greater than the torque necessary to unscrew the biostimulator without such a feature. In some embodiments, the torque necessary to unscrew the biostimulator from tissue is greater than the torque necessary to either further screw, engage, or re-engage the biostimulator into tissue. When an anti-unscrewing feature provides this function, the chances of a biostimulator accidentally unscrewing or disengaging itself from the tissue is reduced. It should be noted that the torque necessary to initially insert a biostimulator into tissue is greater due to the puncturing or piercing of tissue and the formation of a helical cavity. Thus, in some embodiments, the anti-unscrewing features need only provide that the torque necessary to unscrew the biostimulator from tissue be greater than the torque necessary to unscrew the biostimulator from tissue after the biostimulator has already been implanted in tissue (i.e., after the tissue has been pierced).

Figure 2A:
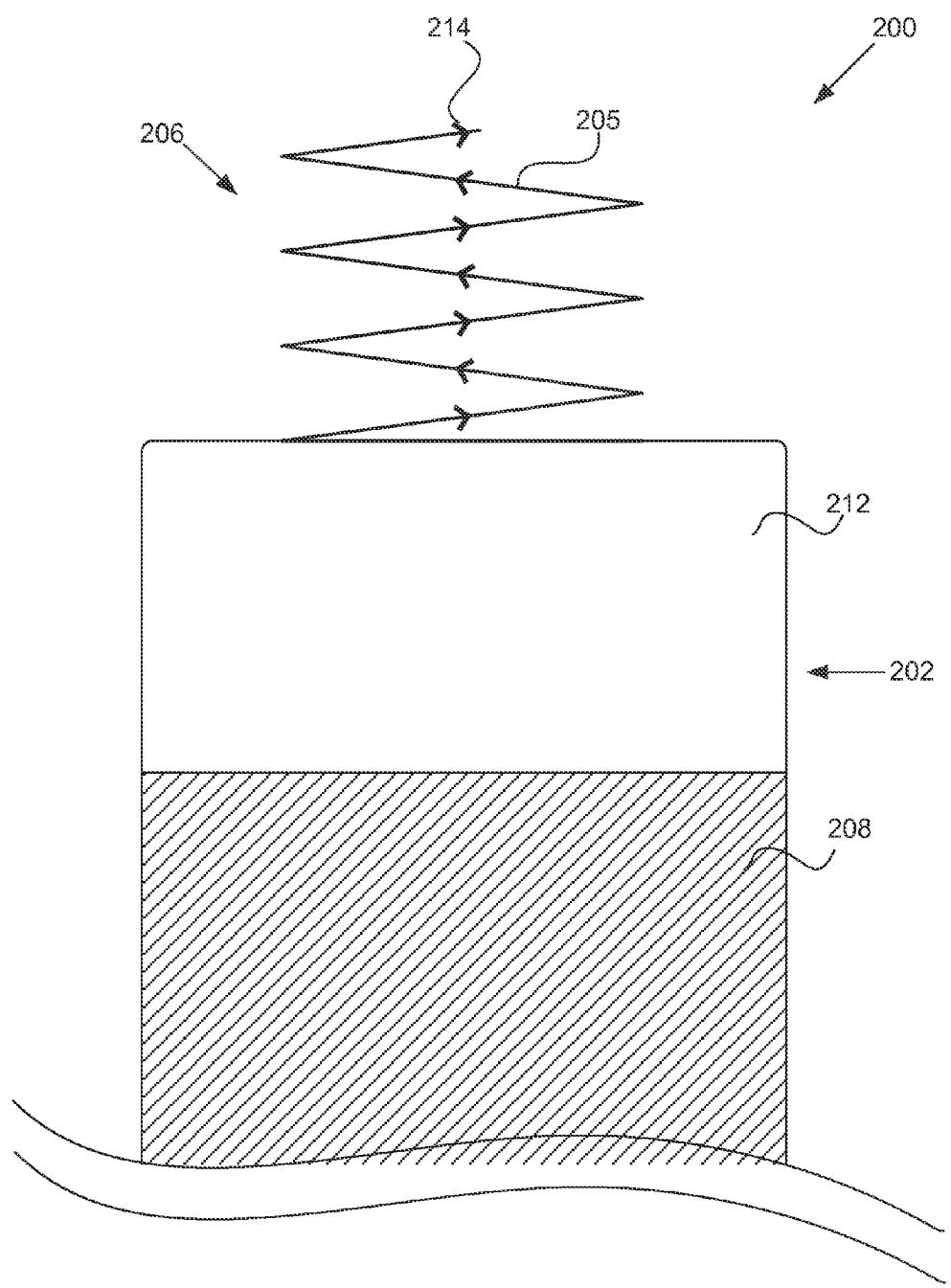
FIGS. 2a-2f illustrate embodiments of anti-unscrewing features disposed on a fixation device of a leadless cardiac pacemaker.

Referring now to FIG. 2a, a leadless biostimulator 200 includes an anti-unscrewing feature disposed on a fixation device and configured to prevent disengagement of the biostimulator from tissue. The biostimulator 200 can be similar to the biostimulator 100 of FIG. 1, and thus housing 202, fixation device 205, electrode 206, insulator 208, and header assembly 212 can correspond, respectively, to housing 102, fixation device 105, electrode 106, insulator 108, and header assembly 112 described above.

Figure 2B:
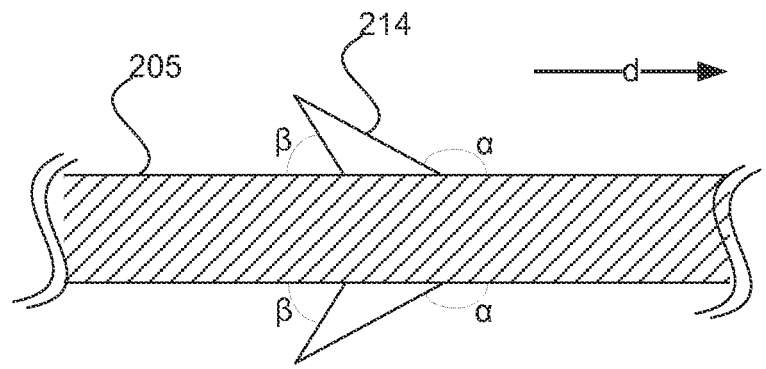

In FIG. 2a, the anti-unscrewing feature can comprise at least one barb 214 disposed on the fixation device 205. Any number of barbs can be positioned along the length of the helix. FIG. 2b shows a close-up version of the barb 214 of FIG. 2a. Referring to FIG. 2b, when the fixation device is inserted into the tissue at a direction d, the barbs 214 can be pointed in the opposite direction to engage the tissue and prevent disengagement of the fixation device from the tissue. More specifically, the barbs can be pointed proximally away from a distal end of the fixation device. In various embodiments, the angles α and β can be adjusted depending on the torque requirements of the particular application. For example, then angles α and β can be adjusted so the torque required to unscrew the device from tissue is larger than the torque required to re-screw or engage into pre-punctured tissue. In some embodiments, α can range from 135 to 180 degrees and β can range from 30 to 135 degrees. Additionally, the size, number, and/or spacing of the barbs on the fixation device can be increased or decreased to accommodate a desired torque requirement. In some embodiments, the barbs extend only a short distance outwards from the fixation device so as to allow the fixation device to screw into and engage tissue without causing excess injury or damage to the tissue. For example, the barbs may extend less than 5 mm or even less than 1 mm outwards from the fixation device. In the embodiment of FIGS. 2a-2b, the barbs are shown on both sides of the fixation device, but in other embodiments the barbs can be disposed on only a single side of the fixation device. In other embodiments, barbs can be radially offset to reduce the cross-sectional profile at any given point along the fixation device.

Figure 2C:
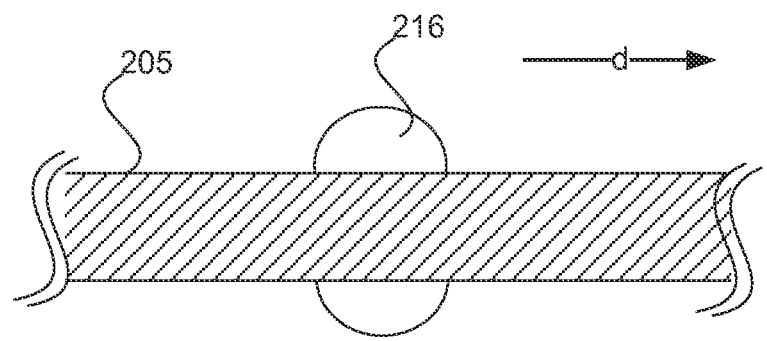
Figure 2D:
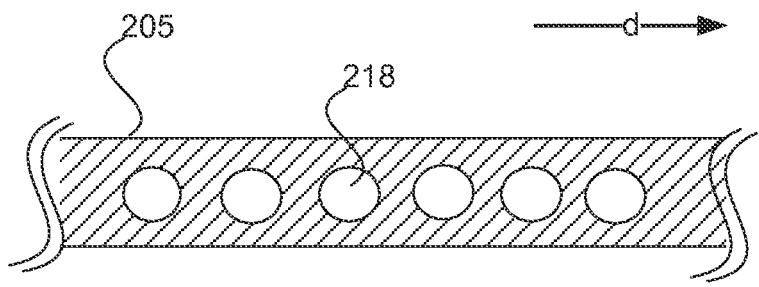
Figure 2E:
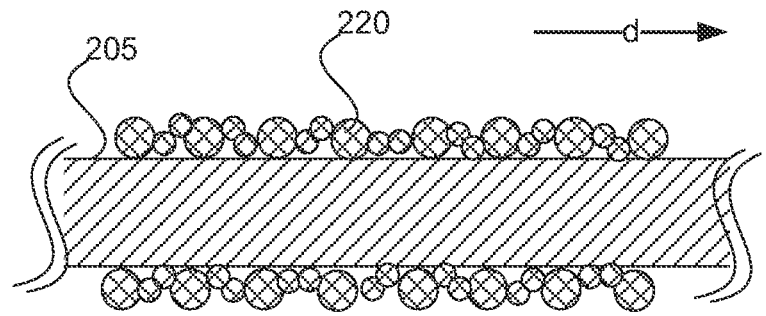

Various other embodiments of anti-unscrewing features disposed on or within the fixation device are illustrated in FIGS. 2c-2e. In FIG. 2c, the anti-unscrewing feature comprises at least one rounded feature 216 disposed on the fixation device 205. The rounded feature can engage tissue when the fixation device is inserted and provide additional resistance to the fixation device to prevent the fixation device from disengaging from the tissue. In some embodiments, the rounded features can range in size from approximately 0.003" to 0.030" in diameter.

Referring to FIG. 2d, the anti-unscrewing feature can comprise at least one cutout or hole 218 in the fixation device 205. The cutouts 218 are configured and sized to allow for tissue ingrowth into the fixation device to prevent the fixation device from disengaging the tissue. In some embodiments, the cutouts 218 extend all the way through the fixation element 205. In other embodiments, the cutouts can be depressions or indents into the fixation element. In some embodiments, the size or diameter of the cutouts can range from approximately 0.001" to 0.010" in diameter.

Referring now to FIG. 2e, the anti-unscrewing feature can comprise of powder or beads 220 disposed on the surface of the fixation device. In some embodiments, the powder or beads can be sintered onto the fixation device to increase the surface area of the fixation device and provide additional friction for preventing the fixation device from disengaging the tissue.

Figure 2F:
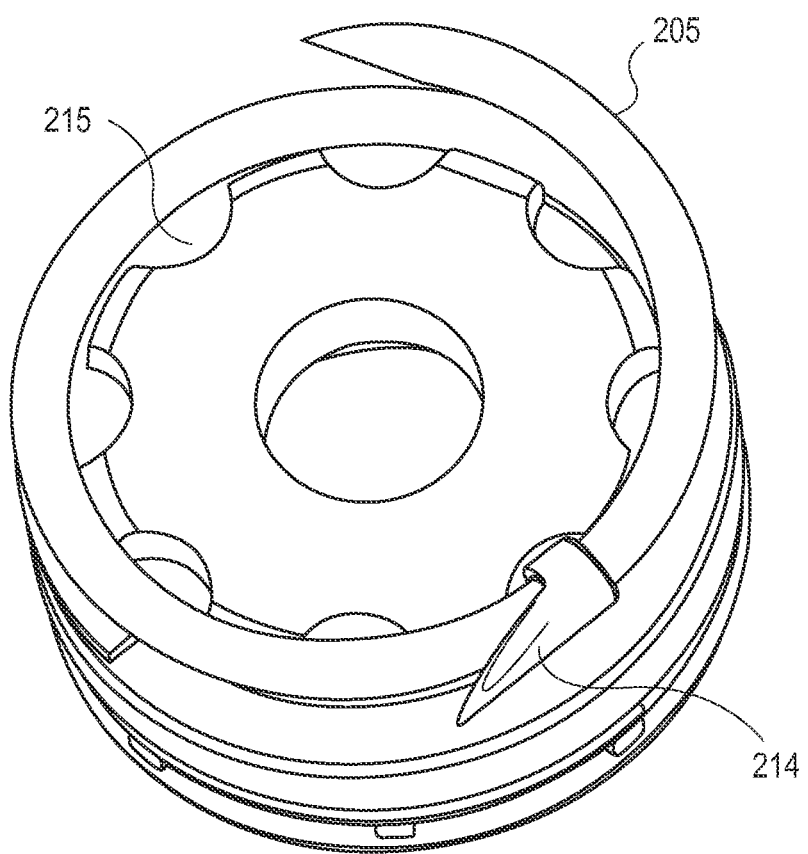

FIG. 2f illustrates another embodiment where an anti-unscrewing feature comprising a barb 214 is combined with scallops 215 (or other cutout features) to promote tissue ingrowth and provide friction preventing anti-rotation.

In some embodiments described above, the anti-unscrewing feature(s) are stamped, cut, welded onto, etched onto, or otherwise attached to or disposed on the fixation device. In one embodiment, the fixation device can be wire-wound and the anti-unscrewing feature(s) can be added onto the fixation device by an additive process. In another embodiment, the fixation device can be subtractively cut from a tube and the anti-unscrewing feature(s) can be formed during the same process.

Figure 3A:
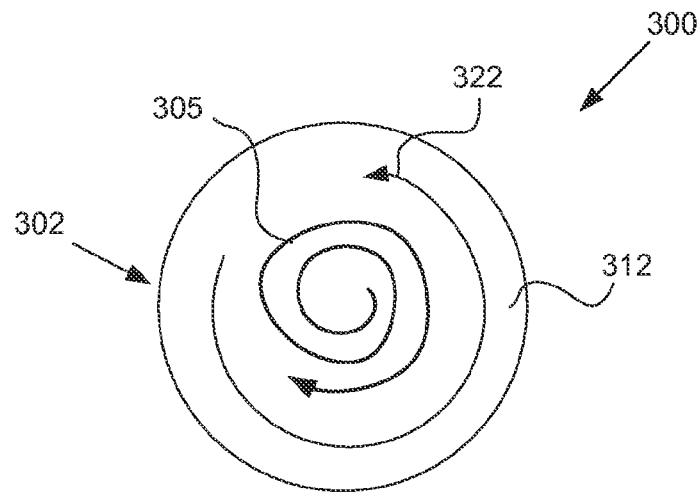
FIGS. 3a-3c illustrate various embodiments of anti-unscrewing helixes on a leadless cardiac pacemaker.
Figure 3B:
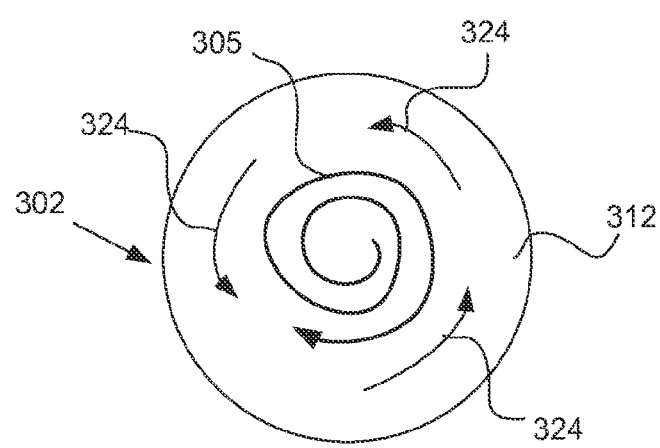
Figure 3C:
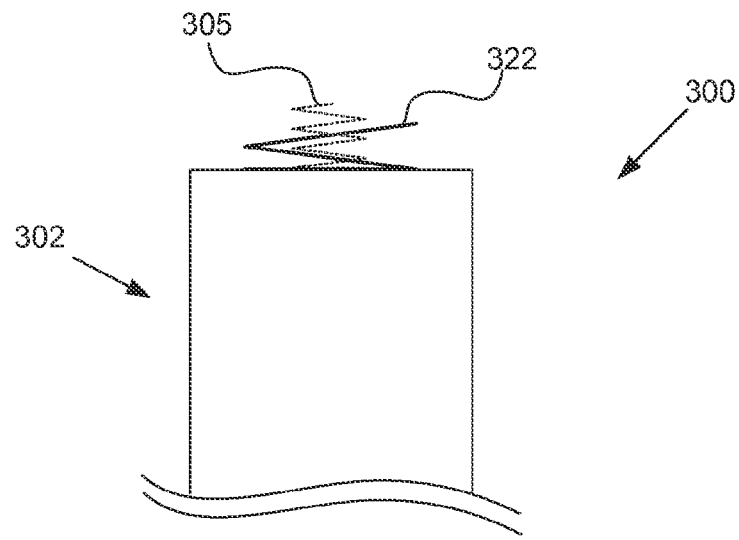

FIGS. 3a-3c illustrate additional embodiments of a anti-unscrewing feature configured to prevent disengagement of a biostimulator from tissue. In contrast to the embodiments described above in FIGS. 2a-2e, where the fixation device or fixation helix itself included an anti-unscrewing feature, the embodiments of FIGS. 3a-3b include an anti-unscrewing feature separate from the fixation device. In FIG. 3a, biostimulator 300 can comprise any of the biostimulators described herein, thus housing 302, fixation device 305, and header assembly 312 can correspond, respectively, to housing 102, fixation device 105, and header assembly 112 of FIG. 1.

Referring to the top-down view of biostimulator 300 in FIG. 3a, it can be seen that fixation device 305 is wound in the clockwise direction, so it follows that biostimulator 300 can be attached to tissue by winding the biostimulator and the fixation helix into tissue in a clockwise direction. The biostimulator 300 can further include an anti-unscrewing feature comprising an anti-unscrewing helix 322. In some embodiments, the anti-unscrewing helix can be positioned outside of the fixation device 305 and wound in the opposite direction of the fixation device (i.e., wound counter-clockwise in FIG. 3a). Thus, if the fixation helix is a right-handed helix then the anti-unscrewing helix is a left-handed helix, and vice versa. Positioning the anti-unscrewing helix outside the fixation device causes any tissue irritation associated with the anti-unscrewing helix to occur away from the fixation device (and away from the active pacing electrode if it is disposed on the fixation helix). In other embodiments, however, the anti-unscrewing helix can be positioned inside the primary fixation device.

The anti-unscrewing helix can be a single helix, double helix, triple helix, etc. In some embodiments, referring to FIG. 3b, the anti-unscrewing feature can comprise a plurality of anti-unscrewing helixes 324, to provide enhanced stability to the overall fixation system. In other embodiments, the anti-unscrewing helix 322 or helixes 324 can include barbs or other anti-unscrewing features, such as those described above in FIGS. 2a-2e. In this example, barbs would only be used if the anti-unscrewing helix is wound in the same direction as the fixation device or helix. Winding an anti-unscrewing helix in the opposite direction of the fixation device can prevent a biostimulator from disengaging tissue because any counter-rotation of the biostimulator would cause the anti-unscrewing helix or helixes to engage the tissue. In some embodiments, the anti-unscrewing helix or helixes can also be used for sensing or for evoked response.

FIG. 3c shows a side-view of the biostimulator 300 of FIG. 3a. From FIG. 3c, it can be seen that the fixation device 305 is longer than the anti-unscrewing helix and extends further from a distal end of the biostimulator than the anti-unscrewing helix 322. This allows the fixation device to engage tissue first during insertion without the anti-unscrewing helix extending into the tissue. Additionally, it can prevent the anti-unscrewing helix from interfering with mapping or electrical measurements prior to fixation of the device into tissue. In some embodiments, the fixation helix can be fully engaged into tissue, and then the biostimulator can be counter-turned to cause the anti-unscrewing helix to also engage the tissue. In some embodiments, the anti-unscrewing helix can compress in the same manner as a spring, allowing the anti-unscrewing helix to compress against tissue when the fixation helix is inserted into tissue. In this embodiment, any scar tissue caused by the anti-unscrewing helix engaging the tissue will be positioned away from the primary fixation device or fixation helix. When the fixation helix comprises an electrode, any scar tissue cased by the anti-unscrewing helix is advantageously positioned away from the electrode. As such, the anti-unscrewing helix is not a secondary fixation element, but rather, will only engage the tissue in the event the biostimulator unscrews or loosens from tissue. In FIG. 3c, the anti-unscrewing helix is shown as being approximately 50% the height of the fixation device. In other embodiments, the anti-unscrewing helix can be any size with respect to the fixation device, however it is typically 25-50% of the height of the fixation device.

FIGS. 4a-4b illustrate additional embodiments of anti-unscrewing features separate from the fixation device or helix. For example, in FIG. 4a, a biostimulator comprising a housing 402, fixation device 405, insulator 408, and header assembly 412 can further include teeth 426 disposed on the top or distal-most surface of the header assembly. In some embodiments, the teeth can be arranged asymmetrically to provide grip and/or resistance only in an unscrewing direction to the fixation device. In FIG. 4b, the header assembly 412 can include a tapered surface 428, and the teeth 426 can be disposed along both the top or distal-most surface and the tapered surface of the header assembly to increase the anti-unscrewing surface area.

Figure 4C:
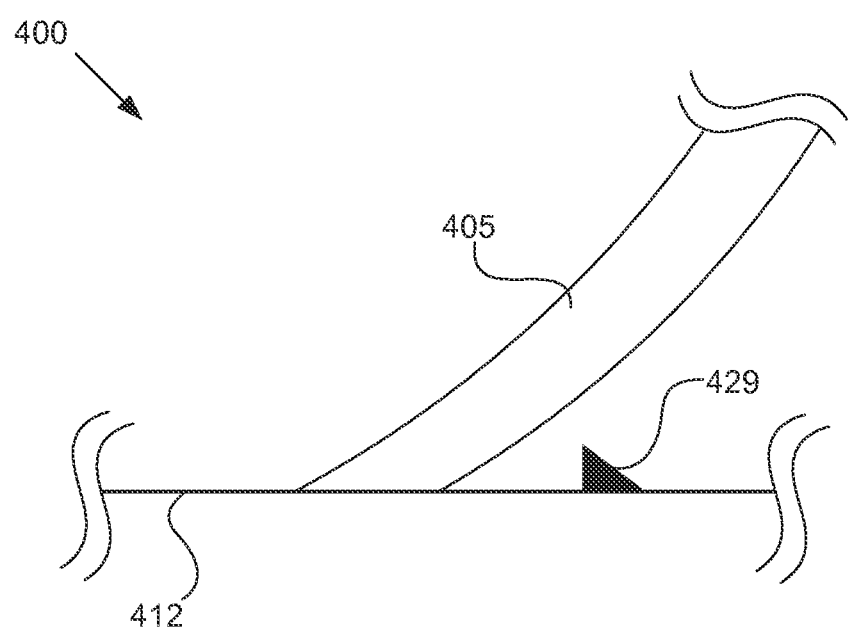

FIG. 4c illustrates yet another embodiment of a biostimulator including an anti-unscrewing feature separate from the fixation device. FIG. 4c is a close-up view of a distal portion of a biostimulator 400, showing header assembly 412 and fixation device 405. In this embodiment, an anti-unscrewing feature can comprise a cleat or wedge 429 positioned on the header assembly in close proximity to where the fixation device 405 joins the header assembly. In FIG. 4c, the cleat resembles a triangle or barb, but other shapes and designs can be used. When the biostimulator is fully affixed to tissue by the fixation device or fixation helix 405, tissue can become wedged between the fixation device and the cleat. When the cleat includes a sharp edge directed towards the fixation device, as shown in FIG. 4c, tissue grabbed by or wedged between the cleat and the fixation device can cause the biostimulator to resist unscrewing and accidental detachment from the tissue. In FIG. 4c, the cleat is shown positioned underneath the fixation device. However, in other embodiments, the cleat or cleats can be positioned on the inside and/or outside surface of the fixation device. All three locations can be used independently or in combination, for example. FIG. 4f illustrates yet another embodiment of a biostimulator having cleats or wedges 429 positioned under the fixation device 405.

In FIGS. 4a-4c, the teeth are shown as pointing straight up or being perpendicular to the biostimulator. However, in other embodiments, the teeth can be angled to one side to increase the ability of the teeth to engage tissue in the event of an unscrewing of the device. For example, if the biostimulator is engaged in a clockwise direction into tissue, the teeth may be angled in the opposite direction on the biostimulator so as to apply additional force on the tissue in the event that the biostimulator is accidentally rotated in the counter-clockwise direction. FIG. 4d illustrates one embodiment of a biostimulator having teeth 426 which apply force in an unscrewing direction opposite the direction that a fixation device 405 is inserted/engaged into tissue.

Figure 4E:
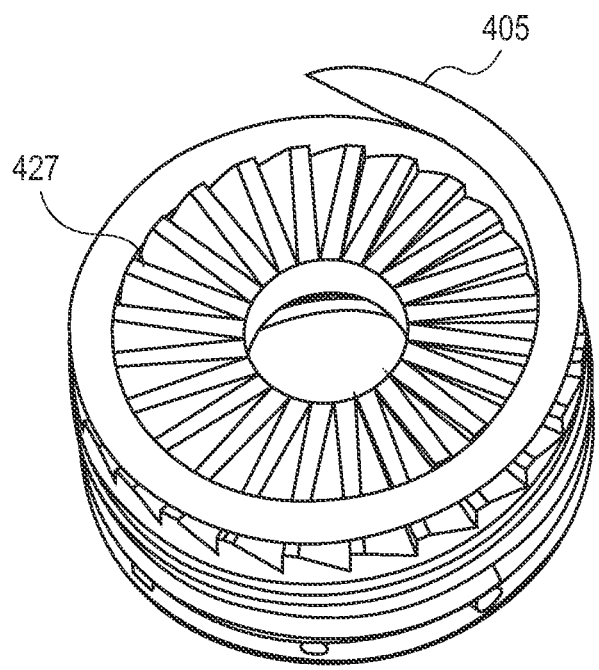
Figure 4F:
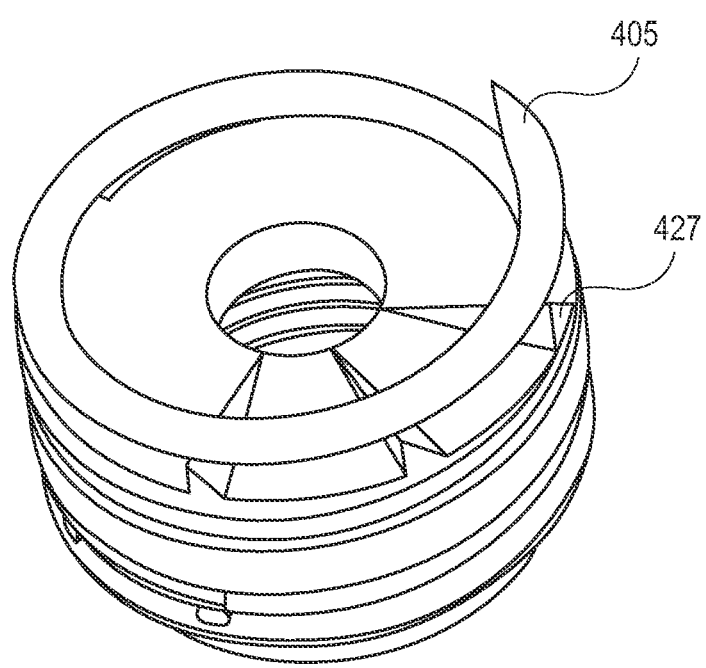

FIG. 4e illustrates another embodiment of a biostimulator having teeth 427 arranged in a radial direction around the biostimulator which are configured to apply force in an unscrewing direction opposite the direction that a fixation device 405 is inserted/engaged into tissue.

Referring now to FIGS. 5a-5k, a biostimulator 500 according to some embodiments can further include an anti-unscrewing feature comprising a tine or tines 530 extending radially from the biostimulator. As before, the biostimulator 500 can include any of the features described herein, including a fixation device 505 and a header assembly 512, among other features.

Figure 5A:
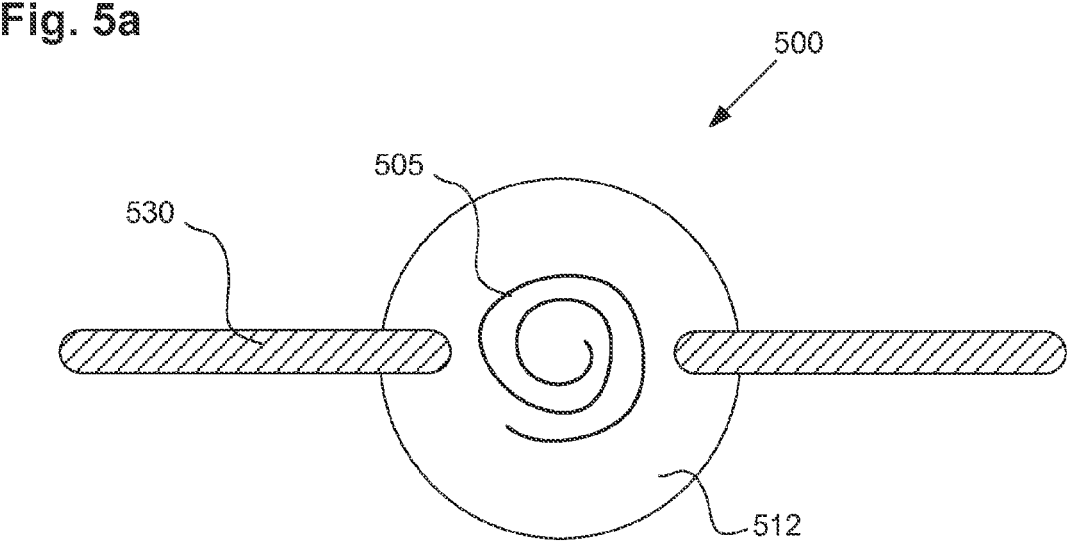
FIGS. 5a-5p illustrate various embodiments of leadless cardiac pacemakers having tine assemblies and anti-unscrewing features.
Figure 5B:
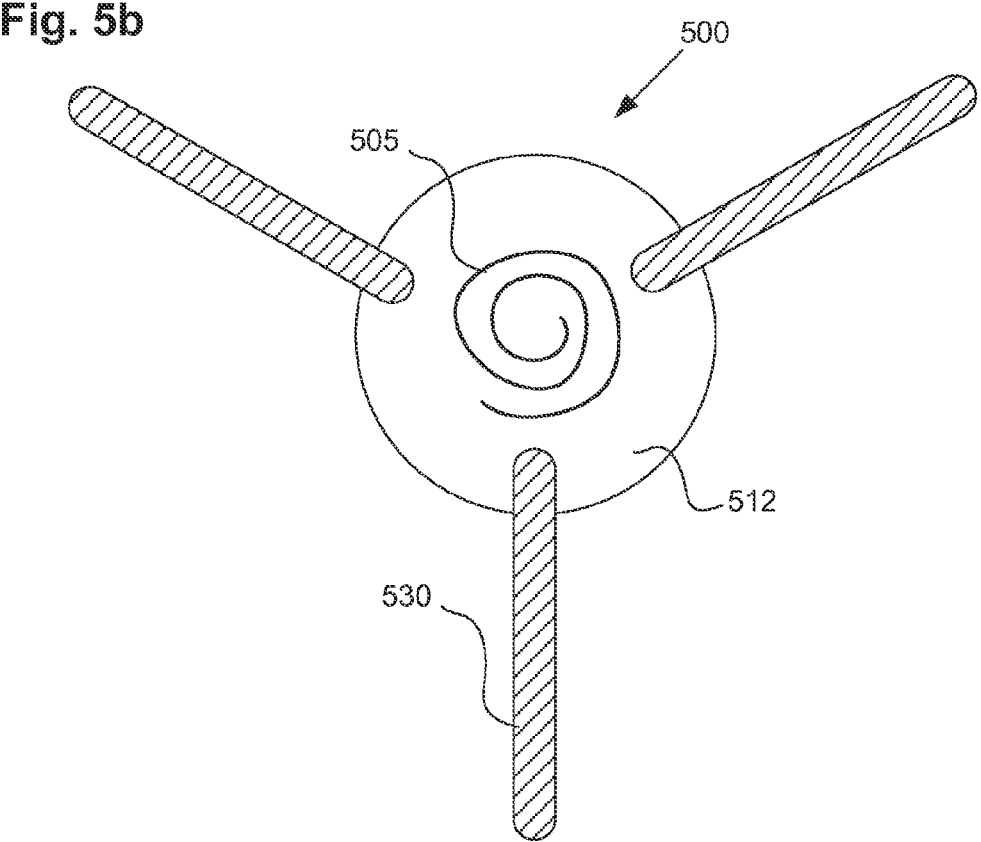

In FIG. 5a, the biostimulator can include two tines 530 disposed on opposite sides of a distal end of the header assembly 512. In some embodiments, the tines can be directed outwards from the biostimulator, perpendicular to a longitudinal axis of the biostimulator. The tines can also be attached at any position on the biostimulator, but typically will be disposed on a distal portion of the biostimulator on or near the header assembly 512. The tines can provide a counter-rotation restorative force to tissue, such as the cardiac wall when the biostimulator is implanted within the heart. Referring to FIG. 5b, the biostimulator can include more than two tines 530 to increase the number of features available to prevent the fixation device from disengaging tissue. The tines 530 can typically comprise materials such as silicone or a soft polyurethane or other bioabsorbable polymer.

Figure 5C:
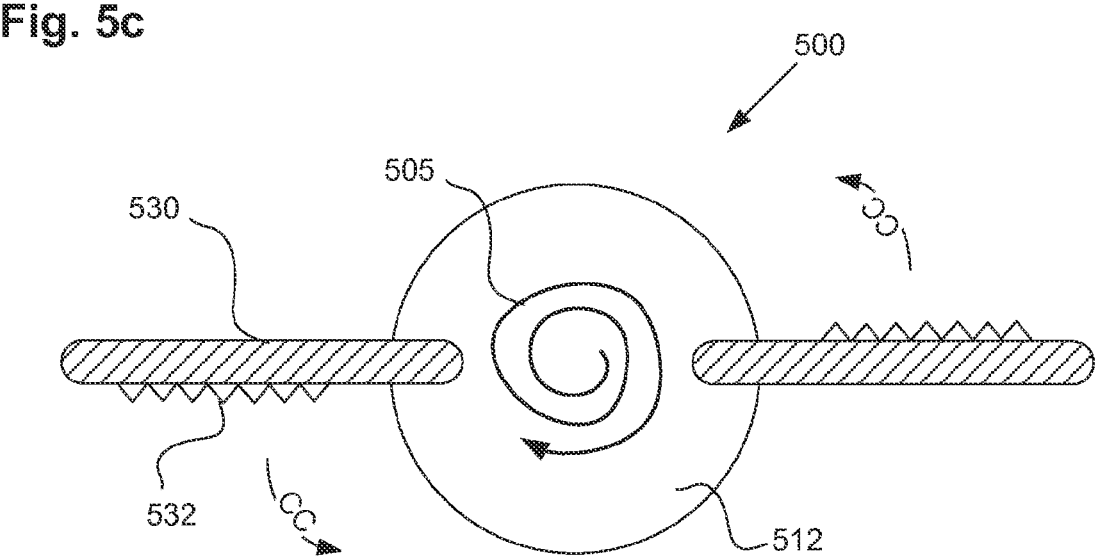

In the embodiment of FIG. 5c, teeth 532 can be molded on the tines 530. In some embodiments, the teeth can be molded all over the surface of the tines, or alternatively, as shown in FIG. 5c, the teeth can be disposed only upon a side of the tines that would engage tissue upon unscrewing of the biostimulator. So in the example of FIG. 5c, if the biostimulator and fixation device are rotated in a clockwise direction to engage the tissue, then the teeth 532 will only engage the tissue to provide counter-rotation torque if the device is rotated in the counter-clockwise direction, as shown by arrows CC. In some embodiments, the tines can comprise a bioabsorbable material.

Figure 5D:
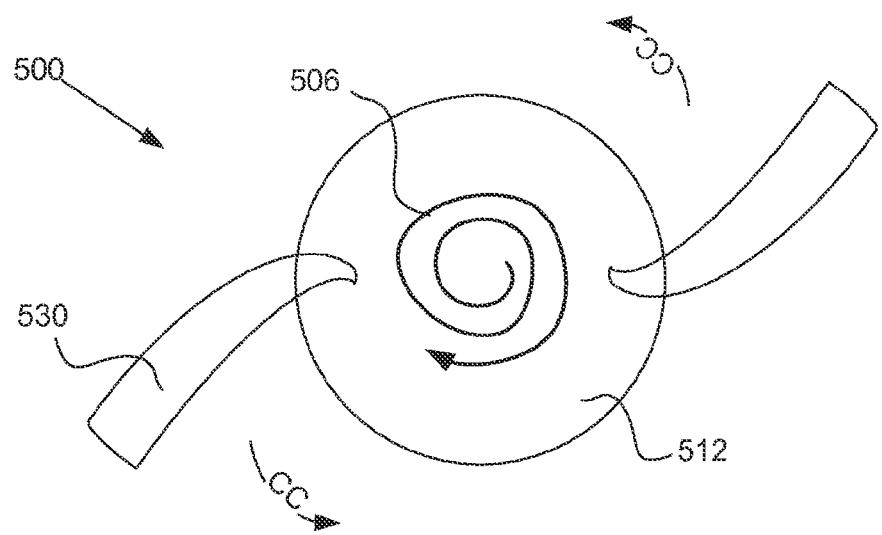

Similarly, in FIG. 5d, the tines 530 can be molded with a spiral shape to provide asymmetrical torque in only one direction. Using the example above where the biostimulator and fixation device are rotated in a clockwise direction to engage the tissue, the spiral shaped tines 530 of FIG. 5d would bend or compress towards the biostimulator during tissue engagement (e.g., clockwise rotation), but would engage the tissue and provide counter-rotation torque to the biostimulator during rotation in the counter-clockwise direction, as indicated by arrows CC.

In FIGS. 5a-5d above, the tines are shown extending outwardly from the biostimulator in a direction perpendicular to a longitudinal axis of the biostimulator. However, referring now to FIG. 5e, it can be seen that the tines can also extend both radially and proximally from the biostimulator. By angling the tines vertically, they can provide vertical traction to aid in anti-unscrewing as well as aid the biostimulator's fixation to tissue. This can be particularly useful in some cardiac situations, such as when the biostimulator is disposed within a ventricle.

Figure 5E:
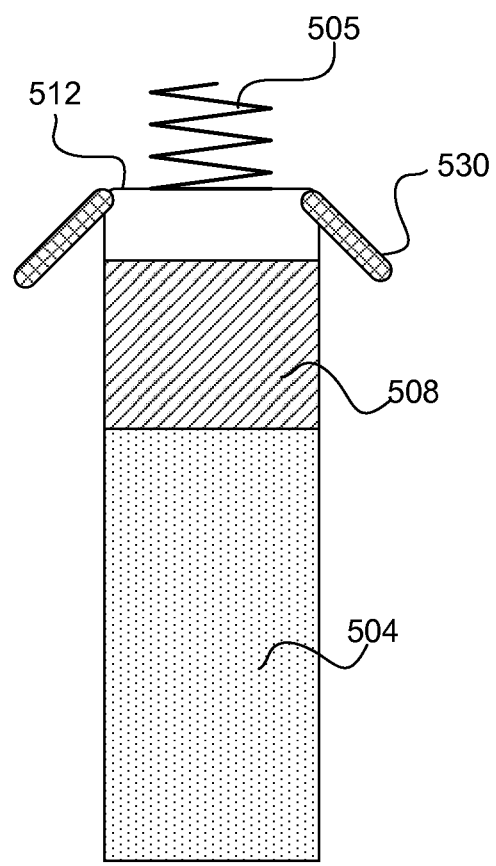
Figure 5F:
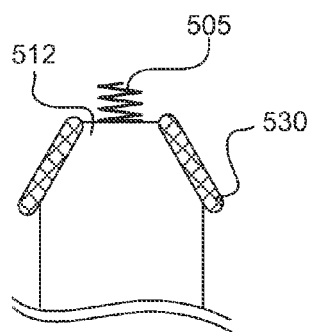
Figure 5I:
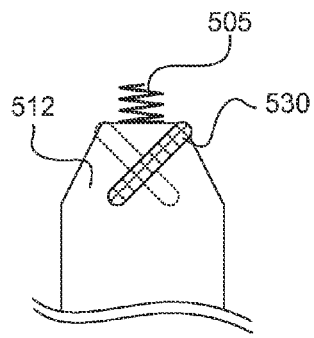
Figure 5G:
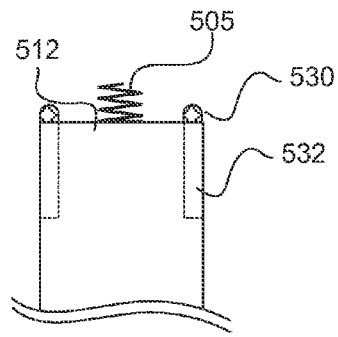
Figure 5J:
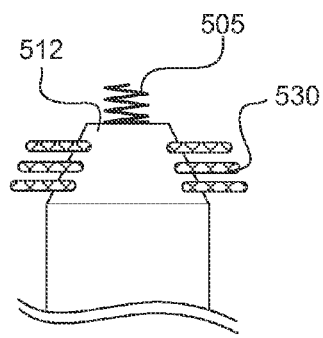
Figure 5H:
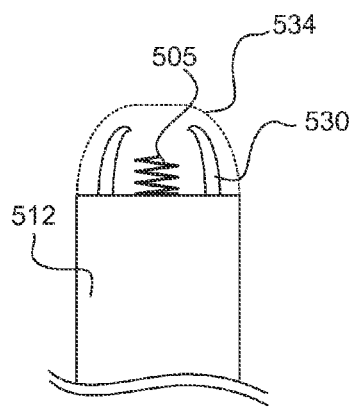

FIGS. 5f-5h illustrate additional embodiments comprising a tine or tines 530 providing anti-unscrewing features to the biostimulator. In FIG. 5f, the tines can fold against the header assembly 512 during insertion of the biostimulator into the body. In some embodiments, the tines can be held in place against the header assembly by an introducer or catheter, for example. When the biostimulator exits the introducer or catheter, the tines can spring outward to assume their anti-unscrewing shape (as shown in FIG. 5a or 5e, for example). The tines can be formed for a shape memory material, such as Nitinol, to assume a pre-determined anti-unscrewing shape. In another embodiment, as shown in FIG. 5g, the tines can fold into cavities 532 disposed within the header assembly 512. In yet another embodiment, as shown in FIG. 5h, a dissolvable capsule 534 (e.g., mannitol, sorbitol, etc) can enclose the fixation device 505 and tines 530 during implantation of the biostimulator. Once the biostimulator is inserted into the body, the mannitol capsule will dissolve, allowing the tines to revert to their anti-unscrewing position.

Figure 5K:
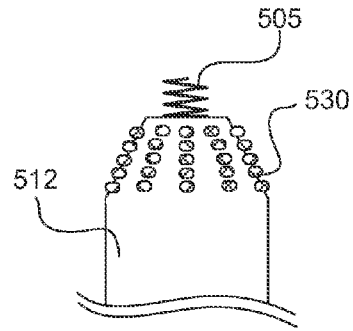

Other tine arrangements are shown in FIGS. 5i-5k. In FIG. 5i, the tines 530 can be folded vertically as well as rotationally around the biostimulator during implantation. In the embodiment of FIG. 5j, multiple tines at various distances from the fixation device 505 can extend outwards from the biostimulator. In FIG. 5k, short and numerous tines 530 can be disposed on the header assembly. These tines can be shaped and angled to provide asymmetrical torque, which means they can provide more rotational friction in one rotational direction (e.g., counter-clockwise) vs. the other direction (e.g., clockwise).

Figure 5M:
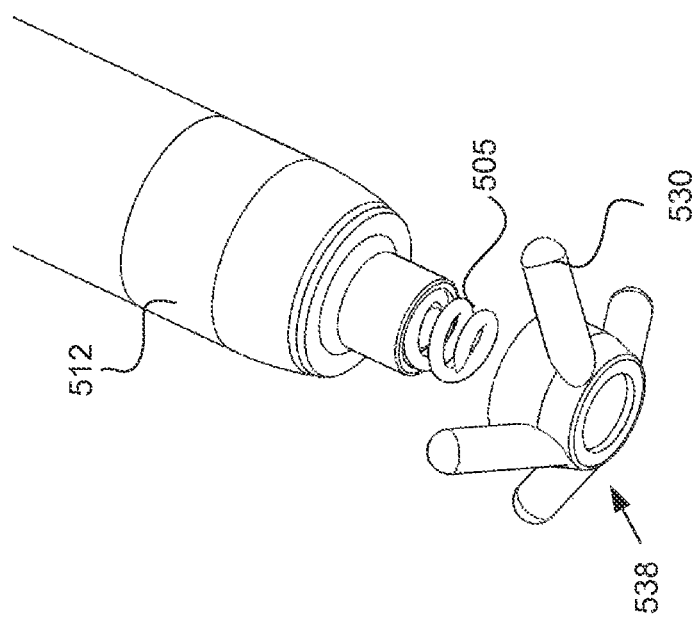

In another embodiment, as shown in FIGS. 5l-5m, tines 530 can be molded as a separate tine assembly 538 and assembled onto the header assembly 512 of the biostimulator via a non-permanent connection such as a compression or snap fit. In vivo, the tines would be fully encapsulated in tissue. If the tines were permanently connected to the biostimulator, this encapsulation would make extraction of the biostimulator very difficult. But in this embodiment, during extraction the biostimulator would separate from the tine assembly 538 and be removed, while the tine assembly would be permanently left behind or abandoned. For example, during an extraction procedure, a pull force would be applied to the biostimulator. Once the pull force exceeds a specified value, the tine assembly would separate from the biostimulator's header assembly. The biostimulator would be subsequently removed and only the encapsulated tine assembly would remain. Therefore, in this embodiment, a fully endothelialized, encapsulated, and permanently fixated tine assembly to cardiac tissue is to be encouraged—it would aid in the clean separation of the biostimulator from the tine assembly and it would prevent an accidental embolization of the tine assembly. In this embodiment, the tines may have design features intended to encourage permanent cardiac fixation, such as increased surface roughness, through holes, surface treatments/coatings, etc. In another embodiment, any of the tines described above can narrow near the biostimulator such that during extraction of the biostimulator the tine can break off or sever from the device.

Figure 5N:
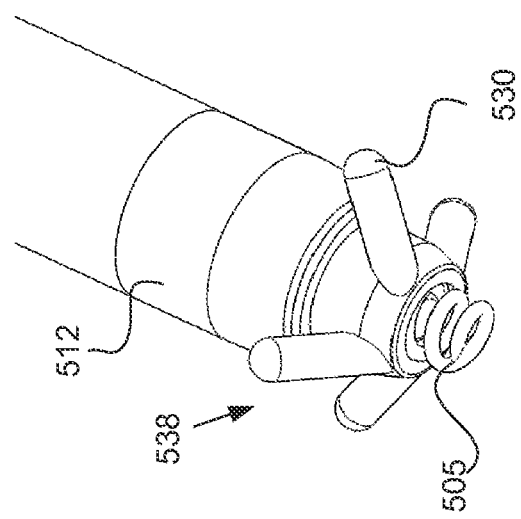
Figure 5N:
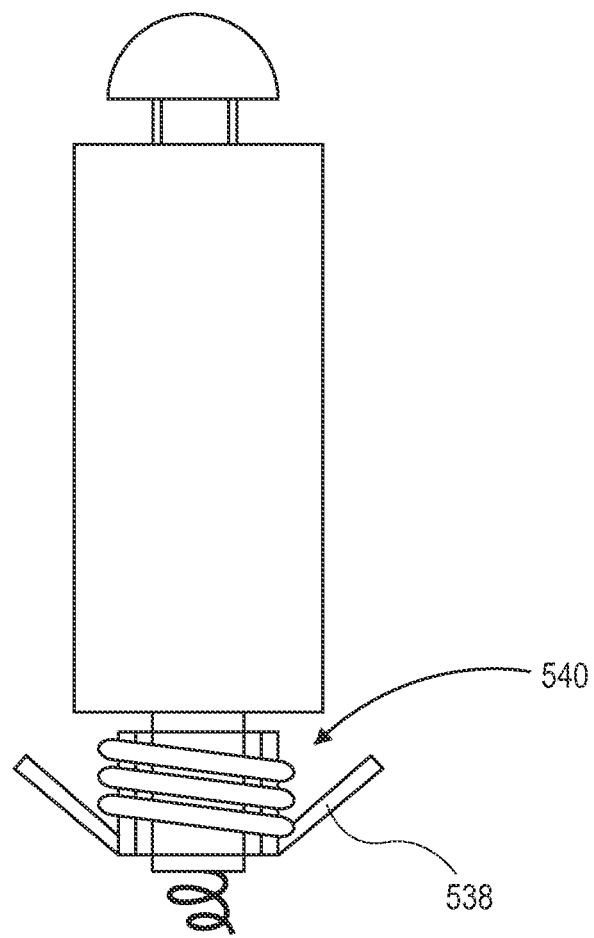
Figure 5O:
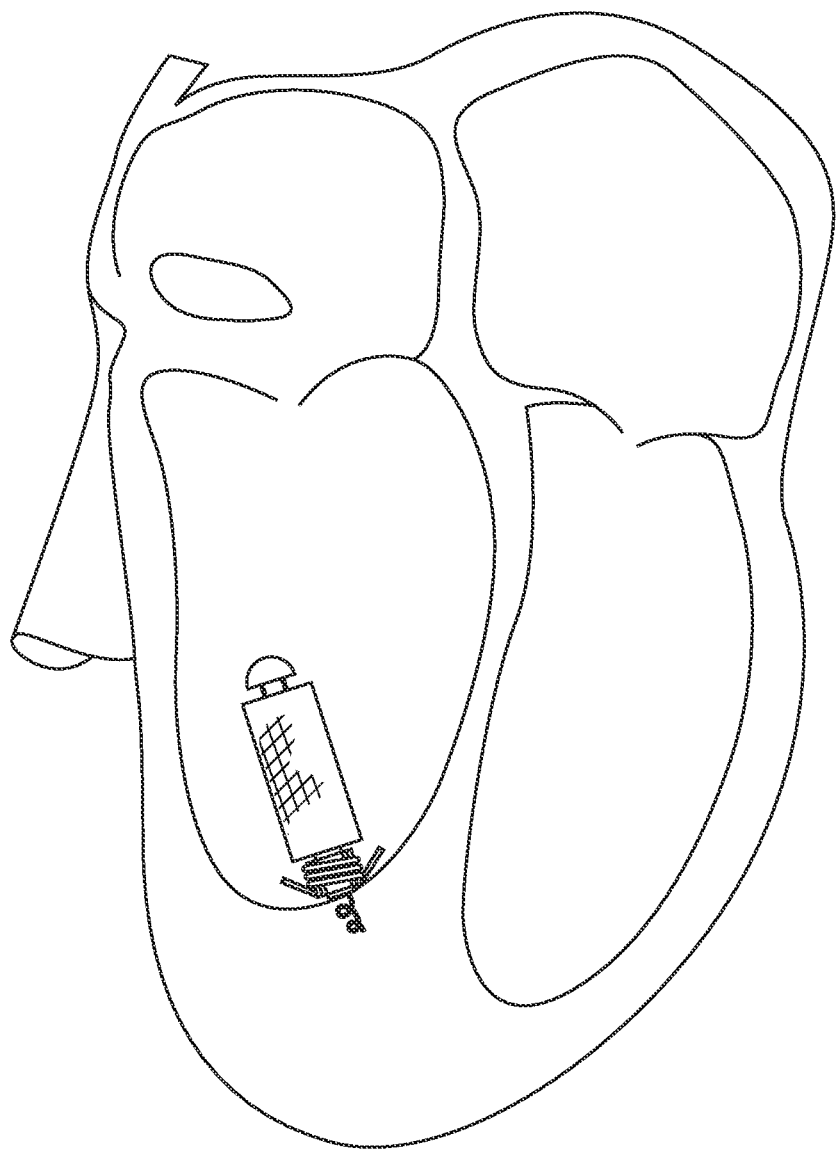
Figure 5P:
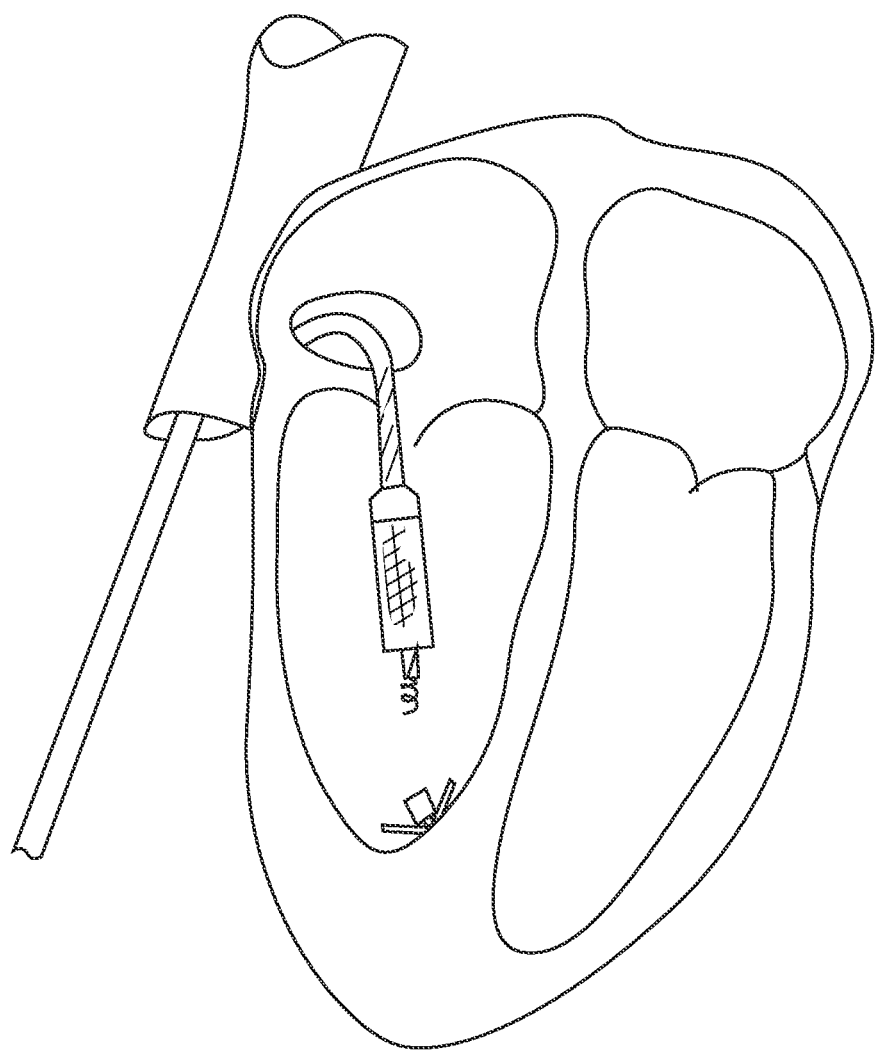

FIG. 5n illustrates a variation of the embodiment shown in FIGS. 5l-5m. In FIG. 5n, tine assembly 538 can be held onto the leadless pacemaker with suture(s) 540. In some embodiments, the sutures can be bio-absorbable to allow the tines to detach from the biostimulator once the suture(s) have been absorbed by tissue. FIG. 5o illustrates a leadless cardiac pacemaker or biostimulator implanted within a chamber of the heart. In this embodiment, the pacemaker can include the suture attached tine assembly described in FIG. 5n. FIG. 5p illustrates a separate retrieval catheter removing the pacemaker of FIG. 5o from the heart after the suture(s) have been absorbed by the tissue. Attaching the tine assembly 538 of FIG. 5n with a bio-absorbable material or suture allows for easier removal of the pacemaker once the suture(s) have dissolved.

Figure 6A:
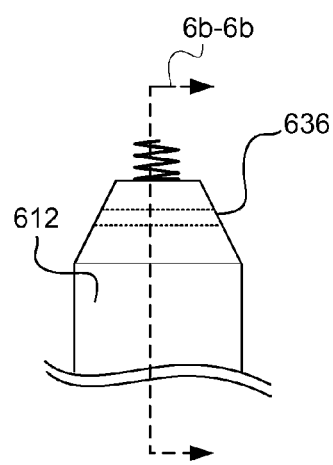
FIGS. 6a-6e illustrate various embodiments of through-hole or partial through-holes incorporated into a leadless cardiac pacemaker.
Figure 6D:
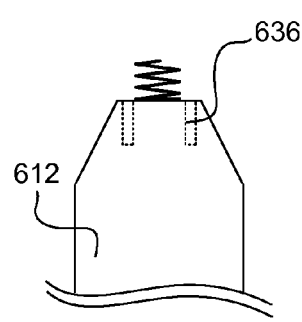
Figure 6B:
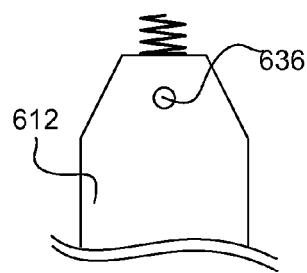
Figure 6E:
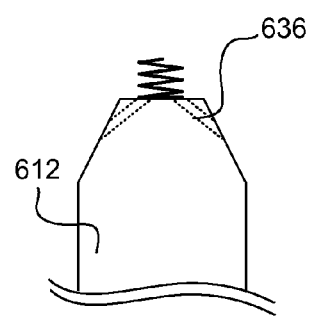

FIGS. 6a-6e illustrate other embodiments of a biostimulator having an anti-unscrewing feature for preventing disengagement of the biostimulator from tissue. In FIG. 6a, a through-hole 636 can extend horizontally through the header assembly 612 to promote tissue in-growth into and across the biostimulator. FIG. 6b is a cross-sectional view of FIG. 6a along line 6b-6b. The relative size of through-hole 636 with respect to the size of the header assembly can be seen in FIG. 6b. In some embodiments, the through-holes can have a diameter of approximately 0.005" to 0.04". Although a single and circular through-hole is illustrated in FIGS. 6a-6b, it should be understood that any number and shape of through-holes can be used in the biostimulator, such as square, rectangular, octagonal, etc. The through-holes can also "neck-down" (i.e., the through-hole can have a narrower diameter towards the center of the device than it does on an outside or perimeter of the device.

Figure 6C:
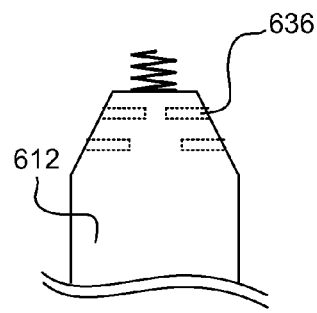

Furthermore, the through-holes do not necessarily have to extend through the entire assembly. Referring to FIG. 6c, the through-holes 636 can extend partially within the header assembly 612. In the embodiment of FIG. 6d, the through holes extend into the header assembly in a vertical direction, instead of the horizontal direction of the through-holes in FIGS. 6a-6c.

Figure 7A:
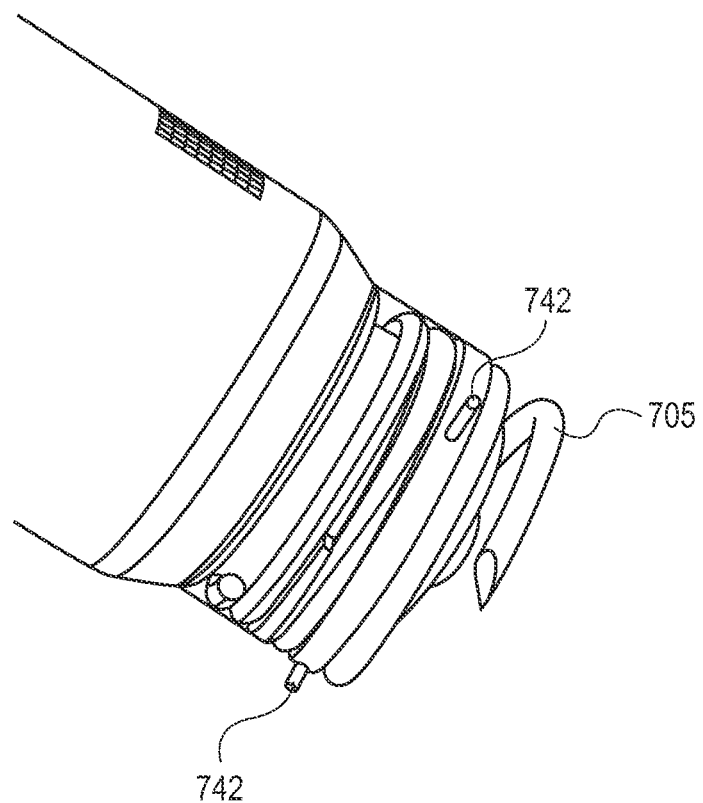
FIGS. 7a-7b illustrate embodiments of a leadless cardiac pacemaker having an anti-unscrewing feature comprising a suture.
Figure 7B:
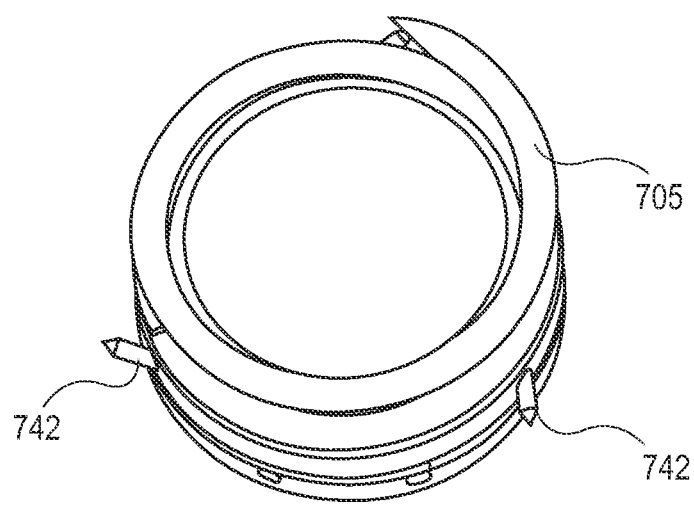

FIGS. 7a-7b illustrate side and top-down views, respectively, of yet another embodiment of a biostimulator having an anti-unscrewing feature for preventing disengagement of the biostimulator from tissue. In FIGS. 7a-7b, the biostimulator can comprise sutures 742 disposed on the biostimulator and/or on fixation device 705. In some embodiments, the sutures can be bio-absorbable. The sutures can be affixed to the biostimulator and/or fixation device by any methods known in the art, such as by mechanical interference, adhesives, soldering, etc. In some embodiments, the sutures can be less than approximately 1-2 mm in length. In other embodiments, the sutures can be larger. The sutures can be configured to bio-absorb in tissue after approximately 30-60 days in some embodiments. In some embodiments, the sutures can be configured to fold against the biostimulator or the fixation device as the biostimulator is inserted into tissue, but the sutures can be configured to expand outwards and engage tissue if the biostimulator and fixation device is unscrewed. As shown in FIG. 7b, in some embodiments the sutures can be applied to point in a direction opposite of the fixation device. Winding the biostimulator in the opposite direction of the fixation device can prevent the biostimulator from disengaging tissue because any counter-rotation of the biostimulator would cause the sutures to engage the tissue.

Features such as cavities and through-holes that promote tissue in-growth into and through the biostimulator can increase fixation of the device to tissue and prevent anti-unscrewing and disengagement of the biostimulator from tissue. Although many of the embodiments described herein include features to promote tissue in-growth, it should be understood that many of the anti-unscrewing features described herein are configured to prevent unintentional detachment of the biostimulator from tissue immediately after implant, but before tissue has had time to grow into the device. In one embodiment, the through-holes are angled with an orifice on a distal face of the biostimulator.

The through-holes described herein can be open and free of any obstructing material, or alternatively, can be filled with a fast-dissolving substance, such as mannitol, or with a slowly bioabsorbable material. The advantage of filling the through-holes or cavities prior to implantation of the biostimulator is that it eliminates the risk of trapped air embolism and cavities that can serve as a nidus for bacterial growth.

The anti-unscrewing features described herein are intended to prevent a biostimulator from unintentionally unscrewing or disengaging from tissue. These features are most critical at the time shortly following implantation of the biostimulator (e.g., within 1-3 months of implantation). After 1-3 months post-implantation, endothelialization will have had sufficient time to occur such that the biostimulator is fully encapsulated by tissue. The probability of a fully encapsulated biostimulator inadvertently unscrewing itself from tissue is assumed to be relatively low.

Features to prevent unscrewing may be designed to be most effective in the short time period post-implant (e.g., within the first 1-3 months after implantation). These anti-unscrewing features can therefore be manufactured out of a bio-absorbable material. Once they are no longer needed to prevent unscrewing of the biostimulator, they can bioabsorb and disappear. Thus, any of the anti-unscrewing features described herein, including tines, barbs, teeth, secondary or anti-unscrewing helixes, and through-holes may be manufactured out of bioabsorbable materials to be absorbed by the body after the initial 1-3 month time period post-implant.

Various other embodiments of anti-unscrewing features disposed on or within the fixation device are illustrated in FIGS. 7a-7c. In FIG. 7a, an anti-unscrewing feature can be wound around the surface of a fixation device. In this embodiment, the anti-unscrewing feature is configured to prevent disengagement of the fixation device from tissue. The anti-unscrewing feature can comprise a wire or other similar material that engages the tissue as the fixation device is inserted into tissue. In some embodiments, the anti-unscrewing feature can comprise a bio-absorbable material.

A fixation device can comprise cut-outs or indentations along the length of the fixation device. The cut-outs can comprise semi-circular cutouts into the fixation device. These cut-outs allow for tissue ingrowth after the fixation device has been inserted into tissue. Although not shown, the cut-outs can comprise other shapes, including triangular, square, rectangular, etc. shaped cut-outs.

Another embodiment of a fixation device includes anti-unscrewing features. A fixation device can include through-holes and barbs. The through-holes can be disposed along the length of the fixation device. In one embodiment of FIG. 7c, the through-holes are disposed along the main surface of the fixation device, and along the narrow edge surface of the fixation device. The disposed only along a distal portion of the fixation device, but in other embodiments, the barbs can be disposed along any or all parts of the fixation device. In some embodiments, the barbs can comprise a bio-absorbable material that dissolves after the fixation device has been inserted into tissue (e.g., 1-3 months after implantation).

In some embodiments of a leadless cardiac pacemaker in the electrode is separate from the fixation device. An electrode is mounted on a flexible arm which extends outwardly from the body of the pacemaker. The flexible arm can extend radially outwards from the pacemaker to provide additional resistance against tissue in the event that the pacemaker begins to unscrew or become dislodged from tissue. The arm can include additional anti-unscrewing features, such as through-holes, barbs, teeth, etc., to further prevent anti-unscrewing. In some embodiments, the flexible arm is flexible in only one direction of rotation (e.g., the direction of rotation that would allow for the leadless pacemaker to unscrew from tissue), and is stiff or non-flexible in the other direction of rotation.

In an alternative embodiment a pacemaker has an electrode nestled within the fixation device. The pacemaker can be attached to tissue by screwing fixation device into the tissue, which brings the electrode into contact with the tissue. Anti-unscrewing features can be added to prevent the pacemaker from accidentally dislodging or unscrewing itself from tissue. The anti-unscrewing features can extend distally from the body of the pacemaker, as shown, to engage tissue as the pacemaker is implanted.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A leadless biostimulator, comprising:
a housing sized and configured to be implanted within a heart of a patient;
a primary fixation helix attached to the housing and configured to affix the housing to a wall of the heart by rotating in a screwing direction; and
an anti-unscrewing feature disposed on the primary fixation helix or the housing, the anti-unscrewing feature angled in a direction opposite the screwing direction of the primary fixation device so that rotation of the primary fixation helix only in an unscrewing direction causes the anti-unscrewing feature to engage the wall of the heart so as to prevent the primary fixation device from disengaging the wall of the heart.

2. The leadless biostimulator of claim 1 wherein the anti-unscrewing feature comprises at least one barb.

3. The leadless biostimulator of claim 2 wherein the at least one barb is pointed generally proximally away from a distal end of the fixation device.

4. The leadless biostimulator of claim 1 wherein the anti-unscrewing feature is at least one rounded feature.

5. The leadless biostimulator of claim 1 wherein the anti-unscrewing feature is a suture.

6. The leadless biostimulator of claim 5 wherein the suture is bio-absorbable.

7. The leadless biostimulator of claim 1 wherein the anti-unscrewing feature is arranged to provide resistance only in an unscrewing direction of the primary fixation device.

8. The leadless biostimulator of claim 2 wherein:
the barb comprises a triangular structure,
the triangular structure has a first and a second outward side with respect to the primary fixation device,
the first outward side forms an angle α with respect to the primary fixation device,
α is from 130 to 180 degrees,
the second outward side forms an angle β with respect to the primary fixation device, and
β is from 30 to 135 degrees.

9. The leadless biostimulator of claim 2 wherein the at least one barb extends less than 5 mm outward from the primary fixation device.

10. The leadless biostimulator of claim 2 wherein the at least one barb extends less than 1 mm outward from the primary fixation device.

11. The leadless biostimulator of claim 2 wherein the anti-unscrewing feature further comprises cutout features configured to promote tissue ingrowth and provide friction.

12. The leadless biostimulator of claim 2 wherein the anti-unscrewing feature further comprises scallops.

13. A leadless biostimulator, comprising:
a housing sized and configured to be implanted within a heart of a patient;
a primary fixation device attached to the housing and configured to affix the housing to a wall of the heart; and
an anti-unscrewing feature disposed on the primary fixation device, the anti-unscrewing feature angled to provide asymmetric torque providing the primary fixation device with more rotational friction in an unscrewing direction than in a screwing direction, so as to prevent the primary fixation device from disengaging the wall of the heart.

14. The leadless biostimulator of claim 13 further comprising at least one through-hole disposed in the housing, the at least one through-hole configured to promote tissue in-growth into the through-hole to prevent the primary fixation device from disengaging the wall of the heart.

15. The leadless biostimulator of claim 13 wherein the anti-unscrewing feature comprises at least one barb.

16. The leadless biostimulator of claim 15 wherein the at least one barb is pointed generally proximally away from a distal end of the fixation device.

17. The leadless biostimulator of claim 13 wherein the anti-unscrewing feature is a suture.

18. The leadless biostimulator of claim 17 wherein the suture is bio-absorbable.

19. The leadless biostimulator of claim 13 wherein the anti-unscrewing feature is angled to provide resistance only in an unscrewing direction of the primary fixation device.

20. A leadless biostimulator, comprising:
a housing sized and configured to be implanted within a heart of a patient;
a primary fixation helix attached to the housing and configured to affix the housing to a wall of the heart in a screwing direction; and
sutures disposed on the primary fixation helix or the housing, the sutures configured to point in a direction opposite the primary fixation helix such that rotation of the housing in an unscrewing direction causes the sutures to engage the wall of the heart so as to prevent the primary fixation helix from disengaging the wall of the heart.

\* \* \* \* \*